(12) United States Patent
Hagiwara et al.

(10) Patent No.: US 9,879,014 B2
(45) Date of Patent: Jan. 30, 2018

(54) METHOD FOR SCREENING SUBSTANCE CAPABLE OF INHIBITING ABNORMAL SPLICING CAUSATIVE OF ONSET OR PROGRESS OF DISEASE

(71) Applicant: KYOTO UNIVERSITY, Kyoto-shi, Kyoto (JP)

(72) Inventors: Masatoshi Hagiwara, Kyoto (JP); Suguru Yoshida, Tokyo (JP); Takamitsu Hosoya, Tokyo (JP)

(73) Assignee: KYOTO UNIVERSITY, Kyoto-Shi, Kyoto (JP)

( * ) Notice: Subject to any disclaimer, the term of this patent is extended or adjusted under 35 U.S.C. 154(b) by 0 days.

(21) Appl. No.: 14/904,609

(22) PCT Filed: Jul. 14, 2014

(86) PCT No.: PCT/JP2014/068691
§ 371 (c)(1),
(2) Date: Jan. 12, 2016

(87) PCT Pub. No.: WO2015/005491
PCT Pub. Date: Jan. 15, 2015

(65) Prior Publication Data
US 2016/0152620 A1    Jun. 2, 2016

(30) Foreign Application Priority Data

Jul. 12, 2013  (JP) .................................. 2013-146891

(51) Int. Cl.
C07D 473/40  (2006.01)
C12Q 1/68    (2006.01)
A61K 31/52   (2006.01)

(52) U.S. Cl.
CPC ............ *C07D 473/40* (2013.01); *A61K 31/52* (2013.01); *C12Q 1/6897* (2013.01); *C12Q 2600/136* (2013.01)

(58) Field of Classification Search
CPC .... A61K 31/52; C07D 473/40; C12C 1/6897; C12C 2600/136
See application file for complete search history.

(56) References Cited

U.S. PATENT DOCUMENTS 4,172,829 A   10/1979   Naito et al.
4,232,155 A   11/1980   Naito et al.
(Continued)

FOREIGN PATENT DOCUMENTS

JP   2002-504553 A    2/2002
WO   WO 99/43676 A2   9/1999
(Continued)

OTHER PUBLICATIONS

Wolff, Manfred E. "Burger's Medicinal Chemistry, 5ed, Part I", John Wiley & Sons, 1995, pp. 975-977.*
(Continued)

*Primary Examiner* — Savitha Rao
(74) *Attorney, Agent, or Firm* — Birch, Stewart, Kolasch & Birch, LLP

(57) ABSTRACT

A compound and a pharmaceutical composition for disease associated with an abnormal splice variant, use of the compound and the pharmaceutical composition, or a screening method of the compound and the pharmaceutical composition are provided. One or more embodiments disclose a compound expressed by the following formula (I) or (I') or prodrugs or pharmaceutically acceptable salts thereof. Another one or more embodiments disclose a screening method using a DNA construct that is fused, arranged, or
(Continued)

constructed so as to express different reporter genes for a wild-type splice variant and an abnormal splice variant that contributes to the development or progression of disease;

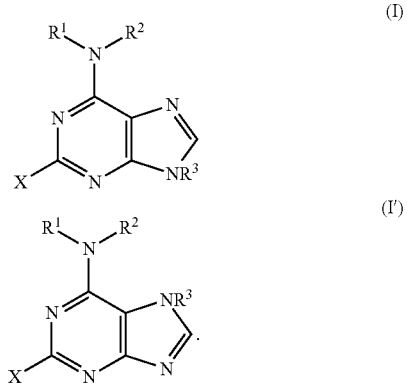

5 Claims, 3 Drawing Sheets

(56) References Cited

U.S. PATENT DOCUMENTS

| | | | |
|---|---|---|---|
| 6,221,873 | B1 | 4/2001 | Havlicek et al. |
| 6,413,974 | B1 | 7/2002 | Dumont et al. |
| 7,737,110 | B2 | 6/2010 | Slaugenhaupt et al. |
| 2006/0014763 | A1 | 1/2006 | Slaugenhaupt et al. |
| 2008/0090849 | A1 | 4/2008 | Bordon-Pallier et al. |

FOREIGN PATENT DOCUMENTS

| | | | |
|---|---|---|---|
| WO | WO 2004/028464 A2 | | 4/2004 |
| WO | WO 2008/073619 A2 | | 6/2008 |
| WO | WO 2010/118367 A2 | | 10/2010 |
| WO | WO2010118367 | * | 10/2010 |
| WO | WO 2010/135664 A1 | | 11/2010 |
| WO | WO 2010/143168 A2 | | 12/2010 |
| WO | WO 2011/152043 A1 | | 12/2011 |
| WO | WO 2014/015291 A1 | | 1/2014 |
| WO | WO 2014/083327 A1 | | 6/2014 |
| WO | WO 2014/134750 A1 | | 9/2014 |

OTHER PUBLICATIONS

Nakamura, I. et al. Transition-Metal-Catalyzed Reactions in Heterocyclic Synthesis. Chem. Rev. 2004, vol. 104, p. 2127.*
Anderson (Chem and Biol 10:787-797, 2003).*
Thiel (Nature Biotechnol 2:513-519, 2004).*
Fedorov et al., "Specific CLK Inhibitors from a Novel Chemotype for Regulation of Alternative Splicing," Chemistry & Biology, vol. 18, Jan. 28, 2011, pp. 67-76.
Muraki et al., "Manipulation of Alternative Splicing by a Newly Developed Inhibitor of CLKs," The Journal of Biological Chemistry, vol. 279, No. 23, Jun. 4, 2004 (first published Mar. 8, 2004), pp. 24246-24254 (10 pages total).
Partial Supplementary European Search Report for European Application No. 14823185.5, dated Nov. 3, 2016.
Zhang et al., "PCBP-1 Regulates Alternative Splicing of the CD44 Gene and Inhibits Invasion in Human Hepatoma Cell Line HepG2 Cells," Molecular Cancer, vol. 9, No. 72, 2010, pp. 1-10.
Dolež et al., "Preparation and biological activity of 6-benzylaminopurine derivatives in plants and human cancer cells," Bioorganic & Medicinal Chemistry, vol. 14, Issue 3, Feb. 1, 2006 (available online Oct. 7, 2005), pp. 875-884.
Extended European Search Report, dated Feb. 27, 2017, for European Application No. 14823185.5.
Leonard et al., "Synthesis of 2-fluoro-6-benzylaminopurine and other purine derivatives," Archives of Biochemistry and Biophysics, vol. 92, Issue 1, Jan. 1, 1961, pp. 33-37.
Novotná et al., "Zinc(II) chlorido complexes of protonated kinetin and its derivatives: Synthesis, properties and X-ray structure of [Zn(Hkinetin)Cla₃]·kinetin," Inorganica Chimica Acta, vol. 365, Issue 1, Jan. 15, 2011 (available online Sep. 21, 2010), pp. 113-118.
Breshears et al. "Purines. VIII. The Aminolysis of Certain Chlorosubstituted Purines", Journal of the American Chemical Society, 1959, 81, 3789-3792.
Christofk et al. "Pyruvate kinase M2 is a phosphotyrosine-binding protein", Nature, vol. 452, Mar. 13, 2008.
Hoyer et al. "Peptide Vectors for the Nonviral Delivery of Nucleic Acids", Accounts of Chemical Hoyer Research, vol. 45, No. 7, 2002, 1048-1056.
International Search Report, issued in PCT/JP2014/068691, dated Oct. 14, 2014.
Kataoka et al. "Modulators for splicing of IKBKAP gene, a responsible gene for Familial dysautonomia", an abstract published at Cold Spring Harbor Asia Conference on RNA Biology, Oct. 8-12, 2012.
Nojima et al. "Herpesvirus protein ICP27 switches PML isoform by altering mRNA splicing", Nucleic Acids Research, Sep. 3, 2009, 1-13.
Written Opinion of the International Searching Authority, issued in PCT/JP2014/068691, dated Oct. 14, 2014.

* cited by examiner

METHOD FOR SCREENING SUBSTANCE CAPABLE OF INHIBITING ABNORMAL SPLICING CAUSATIVE OF ONSET OR PROGRESS OF DISEASE

TECHNICAL FIELD

The present invention relates to a method for screening a substance capable of inhibiting abnormal splicing that contributes to the development or progression of disease, a pharmaceutical composition, and a kit.

BACKGROUND ART

Patent Document 1 discloses a reporter system that can detect alternative splicing, and a method for identifying a compound that affects alternative splicing by using the reporter system.

PRIOR ART DOCUMENTS

Patent Documents

Patent Document 1: WO 2011/152043 A1

DISCLOSURE OF INVENTION

Problem to be Solved by the Invention

Familial dysautonomia (FD) is a congenital fatal disease, i.e., an autosomal recessive inherited disease characterized by sensory and autonomic nerve dysfunctions due to abnormal development, degeneration, and deterioration of nerves. The majority of FD patients have a single base substitution (IVS20$^{+6T \to C}$ mutation) in intron 20 of the IKBKAP (inhibitor of kappa light polypeptide gene enhancer in B cells, kinase complex-associated protein) gene (see FIG. 1A). Such a mutation causes abnormal splicing (exon skipping) that generates an mRNA from which exon 20 is excluded mainly in the nervous system tissue, and thus interferes with the production of normal IKBKAP protein. This results in the above disease (see FIG. 1A).

U.S. Pat. No. 7,737,110 discloses that kinetin, which is a cytokinin, can inhibit abnormal splicing of the IKBKAP gene with the IVS20$^{+6T \to C}$ mutation.

The pyruvate kinase M(PKM) gene undergoes mutually exclusive splicing of exons 9 and 10. When exon 9 is retained, the product is PKM1 mRNA, and PKM1 protein isoform is produced. When exon 10 is retained, the product is PKM2 mRNA, and PKM2 protein isoform is produced. The expression of these isoforms is tissue specific, and PKM1 is expressed in cells with high energy demand such as neurons and muscle cells. On the other hand, PKM2 is expressed in most cancers, organs with high cell proliferation, and undifferentiated cells (see FIG. 5).

In an environment that recapitulates cancer progression in vivo, e.g., hypoxia, the proliferation potency of cells in which the PKM2 isoform is expressed is higher than that of cells in which the PKM1 isoform is expressed. The transfer experiments of tumor cells in which each of the isoforms is expressed show that a tumor with the expression of the PKM2 isoform is significantly larger than that with the expression of the PKM1 isoform (Chrisofk et al., Nature (Letters) 2008).

Herpes simplex virus type 2 (HSV-2) is known to switch the expression of promyelocytic leukemia (PML) isoforms by modifying alternative splicing of the cells infected with HSV-2 (Nojima et al, Nucleic Acid Research, 2009).

In one or more embodiments, the present disclosure provides a compound and a pharmaceutical composition for genetic disease, cancer, infectious disease, or the like, use of the compound and the pharmaceutical composition, and a screening method of the compound and the pharmaceutical composition. In another one or more embodiments, the present disclosure provides a compound and a pharmaceutical composition for familial dysautonomia, use of the compound and the pharmaceutical composition, and a screening method of the compound and the pharmaceutical composition.

Means for Solving Problem

In one or more embodiments, the present disclosure relates to a compound expressed by the following formula (I) or (I') or prodrugs or pharmaceutically acceptable salts thereof.

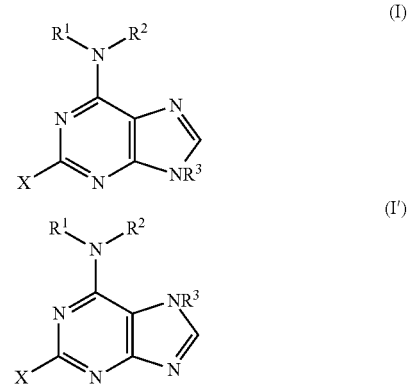

(where, in the formulas (I) and (I'), $R^1$ and $R^2$ each independently represent a hydrogen atom, a linear, branched, or cyclic alkyl group having 1 to 6 carbon atoms, a benzyl or heteroarylmethyl group, a substituted or unsubstituted aryl group, or a substituted or unsubstituted heteroaryl group, $R^3$ represents a hydrogen atom, a linear, branched, or cyclic alkyl group having 1 to 6 carbon atoms, a benzyl or heteroarylmethyl group, a substituted or unsubstituted aryl group, a substituted or unsubstituted heteroaryl group, or $CH_2OC(O)R^4$—, $R^4$ represents a linear, branched, or cyclic alkyl group having 1 to 6 carbon atoms, a benzyl or heteroarylmethyl group, a substituted or unsubstituted aryl group, or a substituted or unsubstituted heteroaryl group, and X represents a hydrogen atom, a halogen atom, an amino group, a $R^1$ and $R^2$ substituted amino group, an azide group, a cyano group, a nitro group, a hydroxyl group, a linear, branched, or cyclic alkyloxy group having 1 to 6 carbon atoms, a substituted or unsubstituted aryloxy group, a substituted or unsubstituted heteroaryloxy group, a mercapto group, a linear, branched, or cyclic alkylthio group having 1 to 6 carbon atoms, a substituted or unsubstituted arylthio group, a substituted or unsubstituted heteroarylthio group, a linear, branched, or cyclic alkyl group having 1 to 6 carbon atoms, a benzyl or heteroarylmethyl group, a substituted or unsubstituted aryl group, or a substituted or unsubstituted heteroaryl group).

In one or more embodiments, the present disclosure relates to a pharmaceutical composition containing the compound expressed by the formula (I) or (I') or the prodrugs or the pharmaceutical acceptable salts of the compound of the present disclosure as an active ingredient.

In one or more embodiments, the present disclosure relates to a pharmaceutical composition for disease in which abnormal splicing contributes to the development or progression of the disease, the pharmaceutical composition containing an active ingredient capable of inhibiting the abnormal splicing.

In one or more embodiments, the present disclosure relates to a method for altering abnormal splicing that contributes to genetic disease in mammalian cells or mammalian individuals, or altering splicing of the pre-mRNA of the mutant IKBKAP gene having the IVS20$^{+6T \to C}$ mutation in human cells or human individuals, a method for increasing the ratio of wild-type splicing to abnormal splicing that contributes to genetic disease in mammalian cells or mammalian individuals, or increasing the ratio of wild-type splicing to abnormal splicing of the pre-mRNA of the mutant IKBKAP gene having the IVS20$^{+6T \to C}$ mutation in human cells or human individuals, or a method for increasing the proportion of exon 20 present in an mRNA that is transcribed from the mutant IKBKAP gene having the IVS20$^{+6T \to C}$ mutation in human cells or human individuals, the method including:

bringing the compound expressed by the formula (I) or (I') or the prodrugs or the pharmaceutically acceptable salts thereof, or the pharmaceutical composition of the present disclosure into contact with human cells or human individuals.

In one or more embodiments, the present disclosure relates to a method for preventing, improving, inhibiting the progression of, and/or treating genetic disease, the method including:

administering the pharmaceutical composition of the present disclosure to a subject in need thereof.

In one or more embodiments, the present disclosure relates to a method for screening a substance capable of inhibiting abnormal splicing that contributes to the development or progression of disease, the method including:

(A) introducing a DNA construct into eukaryotic cells or eukaryotes so that the eukaryotic cells or the eukaryotes, into which the DNA construct has been introduced, are optionally used as conditions for the abnormal splicing to occur, wherein the DNA construct is fused, arranged, or constructed so as to express different reporter genes for a wild-type splice variant and an abnormal splice variant that contributes to the development or progression of disease;

(B) contacting or expressing a test substance with or in the eukaryotic cells or the eukaryotes;

(C) detecting at least one of wild-type splicing and abnormal splicing by expression of the reporter genes; and (D) determining whether the ratio of the expression of the reporter gene by wild-type splicing to the expression of the reporter gene by abnormal splicing is changed as compared to the control that does not contact with or express the test substance.

In one or more embodiments, the present disclosure relates to a method for testing whether a substance inhibits abnormal splicing that results from the IVS20$^{+6T \to C}$ mutation in the IKBKAP gene, the method including:

(A) introducing a DNA construct into eukaryotic cells or eukaryotes, wherein the DNA construct includes a gene that contains an exon a of 3n+1 or 3n+2 bases in length and an intron having a IVS20$^{+6T \to C}$ mutation in the IKBKAP gene, and two different reporter genes, and the gene and the two reporter genes in the DNA construct are fused, arranged, or constructed so as to express different reporter genes for a wild-type splice variant containing the exon a and an abnormal splice variant in which the exon a is skipped;

(B) contacting or expressing a substance to be tested with or in the eukaryotic cells or the eukaryotes;

(C) detecting at least one of wild-type splicing and abnormal splicing by expression of the reporter genes; and (D) determining whether the ratio of the expression of the reporter gene by wild-type splicing to the expression of the reporter gene by abnormal splicing is changed as compared to the control that does not contact with the substance to be tested.

In one or more embodiments, the present disclosure relates to a kit including: a DNA construct that is fused, arranged, or constructed so as to express different reporter genes for a wild-type splice variant and an abnormal splice variant that contributes to the development or progression of disease; and cells that may cause abnormal splicing.

In one or more embodiments, the present disclosure relates to a DNA construct including: a gene that contains an exon a of 3n+1 or 3n+2 bases in length and an intron having the IVS20$^{+6T \to C}$ mutation in the IKBKAP gene; and two different reporter genes, wherein the gene and the two reporter genes in the DNA construct are fused, arranged, or constructed so as to express different reporter genes for a wild-type splice variant containing the exon a and an abnormal splice variant in which the exon a is skipped.

BRIEF DESCRIPTION OF DRAWINGS

FIG. 2 illustrates an example of the results. Normally spliced products are observed in the cells into which the wild-type reporter construct has been transfected, and abnormally spliced products are observed in the cells into which the FD-type reporter construct has been transfected.

FIG. 3 illustrates the results. Compound 1 increases the GFP/RFP ratio in a concentration-dependent manner with the effect of compound 1 superior to that of kinetin.

FIG. 4 shows the results. The addition of compound 1 reduces the abnormal splicing products and increases the normal splicing products with the effect of compound 1 superior to that of kinetin.

DESCRIPTION OF THE INVENTION

Figure 1A:
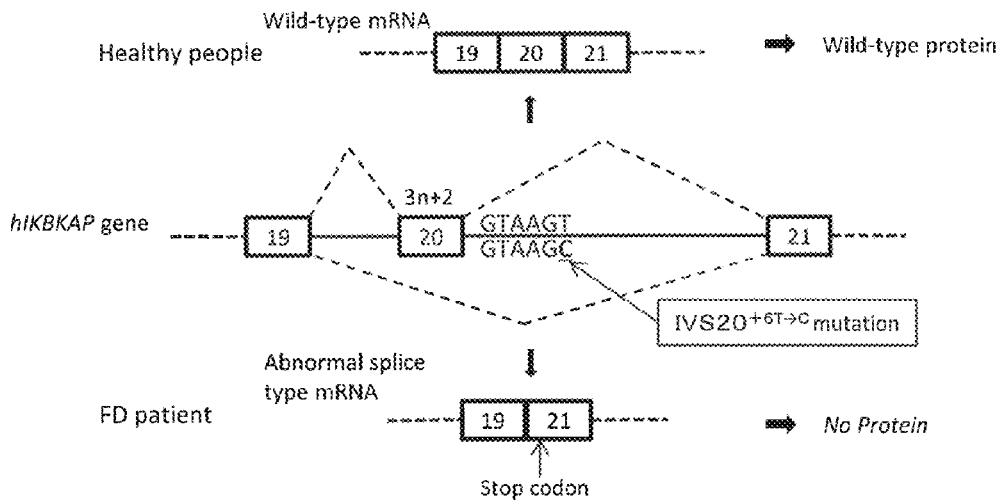
FIG. 1A is a diagram illustrating a single base substitution (IVS20$^{+6T \to C}$ mutation) in intron 20 of the IKBKAP gene found in the majority of familial dysautonomia (FD) patients. The IVS20$^{+6T \to C}$ mutation causes abnormal splicing (exon skipping) mainly in the nervous tissue, and thus interferes with the production of normal IKBKAP protein. This results in FD.

Compound Expressed by General Formula (I) or (I')

In an aspect, the present disclosure relates to a compound expressed by the following formula (I) or (I') or prodrugs or pharmaceutically acceptable salts thereof.

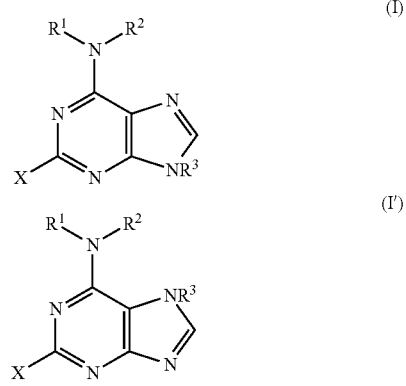

In the formula (I) or (I'), $R^1$ and $R^2$ each independently represent a hydrogen atom, a linear, branched, or cyclic alkyl group having 1 to 6 carbon atoms, a benzyl or heteroarylmethyl group, a substituted or unsubstituted aryl group, or a substituted or unsubstituted heteroaryl group.

In one or more embodiments, examples of the linear or branched alkyl group having 1 to 6 carbon atoms represented by $R^1$ and $R^2$ include the following: a methyl group; an ethyl group; a 1-propyl group; a 2-propyl group; a 2-methyl-1-propyl group; a 2-methyl-2-propyl group; a 1-butyl group; a 2-butyl group; a 1-pentyl group; a 2-pentyl group; a 3-pentyl group; a 2-methyl-1-butyl group; a 3-methyl-1-butyl group; a 2-methyl-2-butyl group; a 3-methyl-2-butyl group; a 2,2-dimethyl-1-propyl group; a 1-hexyl group; a 2-hexyl group; a 3-hexyl group; a 2-methyl-1-pentyl group; a 3-methyl-1-pentyl group; a 4-methyl-1-pentyl group; a 2-methyl-2-pentyl group; a 3-methyl-2-pentyl group; a 4-methyl-2-pentyl group; a 2-methyl-3-pentyl group; a 3-methyl-3-pentyl group; a 2,3-dimethyl-1-butyl group; a 3,3-dimethyl-1-butyl group; a 2,2-dimethyl-1-butyl group; a 2-ethyl-1-butyl group; a 3,3-dimethyl-2-butyl group; and a 2,3-dimethyl-2-butyl group. In one or more embodiments, examples of the cyclic alkyl group having 1 to 6 carbon atoms represented by $R^1$ and $R^2$ include cyclopropyl, cyclobutyl, cyclopentyl, and cyclohexyl.

In one or more embodiments, examples of the heteroaryl (including heteroaryl of the heteroarylmethyl group) represented by $R^1$ and $R^2$ include the following: a 5- to 6-membered monocyclic group containing 1 to 2 nitrogen atom(s); a 5- to 6-membered monocyclic group containing 1 to 2 nitrogen atom(s) and either 1 oxygen atom or 1 sulfur atom; a 5-membered monocyclic group containing 1 oxygen atom or 1 sulfur atom; and a bicyclic group that contains 1 to 4 nitrogen atom(s) and is formed by the condensation of a 6-membered ring and a 5- or 6-membered ring. In another one or more embodiments, examples of the heteroaryl include the following: 2-pyridyl; 3-pyridyl; 4-pyridyl; 2-thienyl, 3-thienyl, 3-oxadiazolyl, 2-imidazolyl, 2-thiazolyl, 3-isothiazolyl, 2-oxazolyl, 3-isoxazolyl, 2-furyl, 3-furyl, 3-pyrrolyl, 2-quinolyl, 8-quinolyl, 2-quinazolinyl, and 8-purinyl. Examples of the aryl group represented by $R^1$ and $R^2$ include an aryl group having 10 or less carbon atoms such as a phenyl group or a naphthyl group.

The number of substituents of the aryl group and the heteroaryl group represented by $R^1$ and $R^2$ may be one or more than one, and the substituents may be either the same or different. In one or more embodiments, examples of the substituent include the following: a halogen atom; a cyano group; a trifluoromethyl group; a nitro group; a hydroxyl group; a methylenedioxy group; a lower alkyl group; a lower alkoxy group; a benzyloxy group; a lower alkanoyloxy group; an amino group; a mono-lower alkylamino group; a di-lower alkylamino group; a carbamoyl group; a lower alkylaminocarbonyl group; di-lower alkylaminocarbonyl group; a carboxyl group; a lower alkoxycarbonyl group; a lower alkylthio group; a lower alkylsulfinyl group; a lower alkylsulfonyl group; a lower alkanoylamino group; and a lower alkylsulfonamide group. In one or more embodiments, the halogen atom may be, e.g., a fluorine atom, a chlorine atom, a bromine atom, or an iodine atom.

In the formula (I) or (I'), $R^3$ represents a hydrogen atom, a linear, branched, or cyclic alkyl group having 1 to 6 carbon atoms, a benzyl or heteroarylmethyl group, a substituted or unsubstituted aryl group, a substituted or unsubstituted heteroaryl group, or $CH_2OC(O)R^4$—.

$R^4$ represents a linear, branched, or cyclic alkyl group having 1 to 6 carbon atoms, a benzyl or heteroarylmethyl group, a substituted or unsubstituted aryl group, or a substituted or unsubstituted heteroaryl group.

In one or more embodiments, examples of the linear or branched alkyl group having 1 to 6 carbon atoms represented by $R^3$ and $R^4$ include the following: a methyl group; an ethyl group; a 1-propyl group; a 2-propyl group; a 2-methyl-1-propyl group; a 2-methyl-2-propyl group; a 1-butyl group; a 2-butyl group; a 1-pentyl group; a 2-pentyl group; a 3-pentyl group; a 2-methyl-1-butyl group; a 3-methyl-1-butyl group; a 2-methyl-2-butyl group; a 3-methyl-2-butyl group; a 2,2-dimethyl-1-propyl group; a 1-hexyl group; a 2-hexyl group; a 3-hexyl group; a 2-methyl-1-pentyl group; a 3-methyl-1-pentyl group; a 4-methyl-1-pentyl group; a 2-methyl-2-pentyl group; a 3-methyl-2-pentyl group; a 4-methyl-2-pentyl group; a 2-methyl-3-pentyl group; a 3-methyl-3-pentyl group; a 2,3-dimethyl-1-butyl group; a 3,3-dimethyl-1-butyl group; a 2,2-dimethyl-1-butyl group; a 2-ethyl-1-butyl group; a 3,3- dimethyl-2-butyl group; and a 2,3-dimethyl-2-butyl group. In one or more embodiments, examples of the cyclic alkyl group having 1 to 6 carbon atoms represented by $R^3$ and $R^4$ include cyclopropyl, cyclobutyl, cyclopentyl, and cyclohexyl.

In one or more embodiments, examples of the heteroaryl (including heteroaryl of the heteroarylmethyl group) represented by $R^3$ and $R^4$ include the following: a 5- to 6-membered monocyclic group containing 1 to 2 nitrogen atom(s); a 5- to 6-membered monocyclic group containing 1 to 2 nitrogen atom(s) and either 1 oxygen atom or 1 sulfur atom; a 5-membered monocyclic group containing 1 oxygen atom or 1 sulfur atom; and a bicyclic group that contains 1 to 4 nitrogen atom(s) and is formed by the condensation of a 6-membered ring and a 5- or 6-membered ring. In another one or more embodiments, examples of the heteroaryl include the following: 2-pyridyl; 3-pyridyl; 4-pyridyl; 2-thienyl, 3-thienyl, 3-oxadiazolyl, 2-imidazolyl, 2-thiazolyl, 3-isothiazolyl, 2-oxazolyl, 3-isoxazolyl, 2-furyl, 3-furyl, 3-pyrrolyl, 2-quinolyl, 8-quinolyl, 2-quinazolinyl, and 8-purinyl. Examples of the aryl group represented by $R^3$ and $R^4$ include an aryl group having 10 or less carbon atoms such as a phenyl group or a naphthyl group.

The number of substituents of the aryl group and the heteroaryl group represented by $R^3$ and $R^4$ may be one or more than one, and the substituents may be either the same or different. In one or more embodiments, examples of the substituent include the following: a halogen atom; a cyano group; a trifluoromethyl group; a nitro group; a hydroxyl group; a methylenedioxy group; a lower alkyl group; a lower alkoxy group; a benzyloxy group; a lower alkanoyloxy group; an amino group; a mono-lower alkylamino group; a di-lower alkylamino group; a carbamoyl group; a lower alkylaminocarbonyl group; di-lower alkylaminocarbonyl group; a carboxyl group; a lower alkoxycarbonyl group; a lower alkylthio group; a lower alkylsulfinyl group; a lower alkylsulfonyl group; a lower alkanoylamino group; and a lower alkylsulfonamide group. In one or more embodiments, the halogen atom may be, e.g., a fluorine atom, a chlorine atom, a bromine atom, or an iodine atom.

In the formula (I) or (I'), X represents a hydrogen atom, a halogen atom, an amino group, a $R^1$ and $R^2$ substituted amino group, an azide group, a cyano group, a nitro group, a hydroxyl group, a linear, branched, or cyclic alkyloxy group having 1 to 6 carbon atoms, a substituted or unsubstituted aryloxy group, a substituted or unsubstituted heteroaryloxy group, a mercapto group, a linear, branched, or cyclic alkylthio group having 1 to 6 carbon atoms, a substituted or unsubstituted arylthio group, a substituted or unsubstituted heteroarylthio group, a linear, branched, or cyclic alkyl group having 1 to 6 carbon atoms, a benzyl or heteroarylmethyl group, a substituted or unsubstituted aryl group, or a substituted or unsubstituted heteroaryl group.

In one or more embodiments, examples of the linear or branched alkyl group having 1 to 6 carbon atoms (including alkyl groups of the alkyloxy group and the alkylthio group) represented by X include the following: a methyl group; an ethyl group; a 1-propyl group; a 2-propyl group; a 2-methyl-1-propyl group; a 2-methyl-2-propyl group; a 1-butyl group; a 2-butyl group; a 1-pentyl group; a 2-pentyl group; a 3-pentyl group; a 2-methyl-1-butyl group; a 3-methyl-1-butyl group; a 2-methyl-2-butyl group; a 3-methyl-2-butyl group; a 2,2-dimethyl-1-propyl group; a 1-hexyl group; a 2-hexyl group; a 3-hexyl group; a 2-methyl-1-pentyl group; a 3-methyl-1-pentyl group; a 4-methyl-1-pentyl group; a 2-methyl-2-pentyl group; a 3-methyl-2-pentyl group; a 4-methyl-2-pentyl group; a 2-methyl-3-pentyl group; a 3-methyl-3-pentyl group; a 2,3-dimethyl-1-butyl group; a 3,3-dimethyl-1-butyl group; a 2,2-dimethyl-1-butyl group; a 2-ethyl-1-butyl group; a 3,3-dimethyl-2-butyl group; and a 2,3-dimethyl-2-butyl group. In one or more embodiments, examples of the cyclic alkyl group having 1 to 6 carbon atoms (including alkyl groups of the alkyloxy group and the alkylthio group) represented by X include cyclopropyl, cyclobutyl, cyclopentyl, and cyclohexyl.

In one or more embodiments, examples of the heteroaryl (including heteroaryl of the heteroaryloxy group, the heteroarylthio group, and the heteroarylmethyl group) represented by X include the following: a 5- to 6-membered monocyclic group containing 1 to 2 nitrogen atom(s); a 5- to 6-membered monocyclic group containing 1 to 2 nitrogen atom(s) and either 1 oxygen atom or 1 sulfur atom; a 5-membered monocyclic group containing 1 oxygen atom or 1 sulfur atom; and a bicyclic group that contains 1 to 4 nitrogen atom(s) and is formed by the condensation of a 6-membered ring and a 5- or 6-membered ring. In another one or more embodiments, examples of the heteroaryl include the following: 2-pyridyl; 3-pyridyl; 4-pyridyl; 2-thienyl, 3-thienyl, 3-oxadiazolyl, 2-imidazolyl, 2-thiazolyl, 3-isothiazolyl, 2-oxazolyl, 3-isoxazolyl, 3-furyl, 3-pyrrolyl, 2-quinolyl, 8-quinolyl, 2-quinazolinyl, and 8-purinyl. Examples of the aryl group (including heteroaryl of the aryloxy group and the arylthio group) represented by X include an aryl group having 10 or less carbon atoms such as a phenyl group or a naphthyl group.

The number of substituents of the aryl group and the heteroaryl group represented by X may be one or more than one, and the substituents may be either the same or different. In one or more embodiments, examples of the substituent include the following: a halogen atom; a cyano group; a trifluoromethyl group; a nitro group; a hydroxyl group; a methylenedioxy group; a lower alkyl group; a lower alkoxy group; a benzyloxy group; a lower alkanoyloxy group; an amino group; a mono-lower alkylamino group; a di-lower alkylamino group; a carbamoyl group; a lower alkylaminocarbonyl group; di-lower alkylaminocarbonyl group; a carboxyl group; a lower alkoxycarbonyl group; a lower alkylthio group; a lower alkylsulfinyl group; a lower alkylsulfonyl group; a lower alkanoylamino group; and a lower alkylsulfonamide group.

In one or more embodiments, the halogen atom represented by X may be, e.g., a fluorine atom, a chlorine atom, a bromine atom, or an iodine atom.

In one or more embodiments, the compound expressed by the formula (I) or (I') does not contain kinetin. In one or more embodiments, $R^1$, $R^2$, $R^3$, $R^4$, and X of the formula (I) or (I') do not make a combination (i.e., a combination of 2-furylmethyl and a hydrogen atom ($R^1$ and $R^2$), a hydrogen atom ($R^3$), and a hydrogen atom (X)) to form kinetin.

In one of more embodiments, when an asymmetric carbon atom and/or a stereoisomer is present, the compound expressed by the formula (I) or (I') may be a mixture of isomers or an isolated isomers.

In one or more embodiments, the "prodrug" of the present disclosure may be a compound that is easily hydrolyzed in a living body to regenerate the compound expressed by the formula (I) or (I'). If a compound has, e.g., a carboxyl group, the prodrug of the compound may be a compound in which the carboxyl group is converted to an alkoxycarbonyl group, a compound in which the carboxyl group is converted to an alkylthiocarbonyl group, or a compound in which the carboxyl group is converted to an alkylaminocarbonyl group. Moreover, if a compound has, e.g., an amino group, the prodrug of the compound may be a compound in which the amino group is substituted with an alkanoyl group to form an alkanoylamino group, a compound in which the amino group is substituted with an alkoxycarbonyl group to form an alkoxycarbonylamino group, a compound in which the amino group is converted to an acyloxymethylamino group, or a compound in which the amino group is converted to hydroxylamine. Further, if a compound has, e.g., a hydroxyl group, the prodrug of the compound may be a compound in which the hydroxyl group is substituted with the acyl group to form an acyloxy group, a compound in which the hydroxyl group is converted to a phosphoric ester, or a compound in which the hydroxyl group is converted to an acyloxymethyloxy group. The alkyl portion of the group used for the conversion to the prodrug may be the alkyl group as described above. The alkyl group may be substituted (e.g., with an alkoxy group having 1 to 6 carbon atoms). In one or more embodiments, e.g., when the prodrug is a compound obtained by converting the carboxyl group to an alkoxycarbonyl group, the compound may include lower alkoxycarbonyl (e.g, having 1 to 6 carbon atoms) such as methoxycarbonyl and ethoxycarbonyl, or lower alkoxycarbonyl (e.g., having 1 to 6 carbon atoms) substituted with an alkoxy group such as methoxymethoxycarbonyl, ethoxymethoxycarbonyl, 2-methoxyethoxycarbonyl, 2-methoxyethoxymethoxycarbonyl, and pivaloyloxymethoxycarbonyl.

The "pharmaceutically acceptable salts" of the present disclosure may include pharmaceutically, pharmacologically and/or medically acceptable salts such as an inorganic acid salt, an organic acid salt, an inorganic base salt, an organic base salt, and an acidic or basic amino acid salt.

Preferred examples of the inorganic acid salt include the following: hydrochloride; hydrobromate; sulfate; nitrate; and phosphate. Preferred examples of the organic acid salt include the following: acetate; succinate; fumarate; maleate; tartrate; citrate; lactate; stearate; benzoate; methanesulfonate; and p-toluenesulfonate.

Preferred examples of the inorganic base salt include the following: alkali metal salts such as sodium salt and potassium salt; alkaline-earth metal salts such as calcium salt and magnesium salt; aluminum salts; and ammonium salts. Preferred examples of the organic base salt include the following: diethylamine salt; diethanolamine salt; meglumine salt; and N,N'-dibenzylethylenediamine salt.

Preferred examples of the acidic amino acid salt include aspartate and glutamate. Preferred examples of the basic amino acid salt include arginine salt, lysine salt, and ornithine salt.

The "salt of the compound" of the present disclosure may include a hydrate that can be formed by allowing the compound to stand in the air so that it absorbs water. Moreover, the "salt of the compound" of the present disclosure may also include a solvate that can be formed by letting the compound absorb some type of solvent.

In one or more embodiments, the compound expressed by the formula (I) or (I') is a compound of the following formula (II):

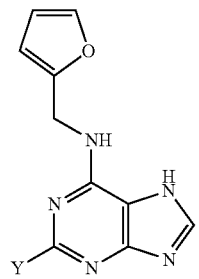

(II)

where, in the formula (II), Y represents a halogen atom. In one or more embodiments, the halogen atom represented by Y may be, e.g., a fluorine atom, a chlorine atom, a bromine atom, or an iodine atom.

[Pharmaceutical Composition]

In an aspect, the present disclosure relates to a pharmaceutical composition containing the compound expressed by the formula (I) or (I') or the prodrug of the compound or the pharmaceutically acceptable salts of the compound and the prodrug as an active ingredient.

In one or more embodiments, the compound expressed by the formula (I) or (I') or the pharmaceutical composition of the present disclosure may be used to inhibit abnormal splicing that contributes to genetic disease. In one or more embodiments, the "abnormal splicing that contributes to genetic disease" of the present disclosure may be abnormal splicing that results from a genetic mutation in a gene to be spliced and is one of the causes of genetic disease.

In one or more non-limiting embodiments, the abnormal splicing that contributes to genetic disease may be, e.g., splicing of a pre-mRNA of the mutant IKBKAP gene having the IVS20$^{+6T \to C}$ mutation that causes familial dysautonomia (FD) (see the above description and FIG. 1A). Many genetic diseases other than FD are known to be caused by abnormal splicing.

Therefore, in one or more embodiments, the compound expressed by the formula (I) or (I') or the pharmaceutical composition of the present disclosure may be used to alter abnormal splicing that contributes to genetic disease in mammalian cells or mammalian individuals. In one or more embodiments, the abnormal splicing that contributes to genetic disease may be abnormal splicing that results from a genetic mutation in a gene to be spliced. In another one or more embodiments, the abnormal splicing that contributes to genetic disease may be splicing of a pre-mRNA of the mutant IKBKAP gene having the IVS20$^{+6T \to C}$ mutation.

In one or more embodiments, the compound expressed by the formula (I) or (I') or the pharmaceutical composition of the present disclosure may be used to increase the ratio of wild-type splicing to abnormal splicing that contributes to genetic disease in mammalian cells or mammalian individuals. In one or more embodiments, the abnormal splicing that contributes to genetic disease may be abnormal splicing that results from a genetic mutation in a gene to be spliced. In another one or more embodiments, the abnormal splicing that contributes to genetic disease may be splicing of a pre-mRNA of the mutant IKBKAP gene having the IVS20$^{+6T \to C}$ mutation.

Thus, in one or more embodiments, the compound expressed by the formula (I) or (I') or the pharmaceutical composition of the present disclosure may be used to alter splicing of a pre-mRNA of the mutant IKBKAP gene having the IVS20$^{\alpha 6T \rightarrow C}$ mutation in human cells or human individuals.

In one or more embodiments, the compound expressed by the formula (I) or (I') or the pharmaceutical composition of the present disclosure may be used to increase the ratio of wild-type splicing to abnormal splicing of a pre-mRNA of the mutant IKBKAP gene having the IVS20$^{+6T \rightarrow C}$ mutation in human cells or human individuals.

Further, in one or more embodiments, the compound expressed by the formula (I) or (I') or the pharmaceutical composition of the present disclosure may be used to increase the proportion of exon 20 present in an mRNA that is transcribed from the mutant IKBKAP gene having the IVS20$^{+6T \rightarrow C}$ mutation in human cells or human individuals.

In one or more embodiments, the mammalian cells or the human cells of this embodiment may include in vivo cells, in vitro cells, or ex vivo cells. In one or more embodiments, the mammalian cells may be human cells or cells of mammals other than human. In one or more embodiments, the human cells may be neurons of human. In one or more embodiments, the human cells and the human individuals of this embodiment may have the IVS20$^{+6T \rightarrow C}$ mutation in the endogenous IKBKAP gene. As illustrated in FIG. 1A, the IVS20$^{+6T \rightarrow C}$ mutation of the present disclosure is a single base substitution (T→C) in intron 20 of the IKBKAP gene. In one or more non-limiting embodiments, whether the human cells and the human individuals have a IVS20$^{+6T \rightarrow C}$ mutation may be determined by a method for detecting a single base substitution. Alternatively, base sequence, array, and various gene amplification methods may be used.

In one or more embodiments, the compound expressed by the formula (I) or (I') or the pharmaceutical composition of the present disclosure may be used to prevent, improve, inhibit the progression of, and/or treat genetic disease in which abnormal splicing contributes to the development or progression of the disease. In one or more embodiments, the compound expressed by the formula (I) or (I') or the pharmaceutical composition of the present disclosure may be used to prevent, improve, inhibit the progression of, and/or treat genetic disease in which abnormal splicing that results from a genetic mutation in a gene to be spliced contributes to the development or progression of the disease.

In one or more embodiments, the compound expressed by the formula (I) or (I') or the pharmaceutical composition of the present disclosure may be used to prevent, improve, inhibit the progression of and/or treat disease associated with abnormal splicing of a pre-mRNA of the mutant IKBKAP gene having the IVS20$^{+6T \rightarrow C}$ mutation.

In one or more embodiments, the compound expressed by the formula (I) or (I') or the pharmaceutical composition of the present disclosure may be used to prevent, improve, inhibit the progression a and/or treat familial dysautonomia (FD).

In one or more embodiments, the "pharmaceutical composition" of the present disclosure may have a dosage form suitable for administration by using the known formulation technology. Specifically, the pharmaceutical composition can be administered orally in dosage forms (but not limited to) such as tablets, capsules, granules, powder, pills, troche, syrups, and liquid formulations. Alternatively, the pharmaceutical composition can be administered parenterally in dosage forms (but not limited to) such as injection, liquid formulations, aerosol, suppositories, patches, cataplasm, lotions, liniments, ointments, and eye drops. These formulations can be produced by a known method using additives (but not limited to) such as excipients, lubricants, binders, disintegrators, stabilizers, corrigents, and diluents.

In one or more embodiments, the pharmaceutical composition of the present disclosure does not contain other active ingredients having a therapeutic effect, or contains another one or more active ingredients.

Examples of the excipient include (but not limited to) the following: starches such as starch, potato starch, and corn starch; lactose; crystalline cellulose; and calcium hydrogen phosphate. Examples of the coating agent include (but not limited to) the following: ethyl cellulose; hydroxypropyl cellulose; hydroxypropyl methylcellulose; shellac; talc; carnauba wax; and paraffin. Examples of the binder include (but not limited to) the following: polyvinyl pyrrolidone; macrogol; and the compounds similar to those given as examples of the excipient. Examples of the disintegrator include (but not limited to) the following: the compounds similar to those given as examples of the excipient; and chemically modified starches and celluloses such as croscarmellose sodium, sodium carboxymethyl starch, and cross-linked polyvinylpyrrolidone. Examples of the stabilizer include (but not limited to) the following: parahydroxybenzoic acid esters such as methylparaben and propylparaben; alcohols such as chlorobutanol, benzyl alcohol, and phenylethyl alcohol; benzalkonium chloride; phenols such as phenol and cresol; thimerosal; dehydroacetic acid; and sorbic acid. Examples of the corrigent include (but not limited to) commonly used sweeteners, acidulants, and flavors.

The preparation of a liquid formulation may use (but not limited to) ethanol, phenol, chlorocresol, purified water, or distilled water as a solvent, and may also use a surface-active agent or an emulsifying agent as needed. Examples of the surface-active agent or the emulsifying agent include (but not limited to) polysorbate 80, polyoxyl 40 stearate, and lauromacrogol.

The method for using the pharmaceutical composition of the present disclosure may differ depending on symptoms, ages, administration methods, etc. The method allows the pharmaceutical composition to be intermittently or continuously administered (but not limited to) orally, endermically, submucosally, subcutaneously, intramuscularly, intravascularly, intracerebrally, or intraperitoneally so that the concentration of the compound (active ingredient) of the formula (I) or (I') in the body is in the range of 100 nM to 1 mM. In a non-limiting embodiment, for oral administration, the pharmaceutical composition may be administered to a subject (e.g., an adult human) in a dosage of 0.01 mg (preferably 0.1 mg) to 2000 mg (preferably 500 mg and more preferably 100 mg), which is expressed in terms of the compound expressed by the formula (I) or (I'), once or several times a day based on the symptom. In a non-limiting embodiment, for intravenous administration, the pharmaceutical composition may be administered to a subject (e.g., an adult human) in a dosage of 0.001 mg (preferably 0.01 mg) to 500 mg (preferably 50 mg) once or several times a day based on the symptom.

[Method and Use]

In another aspect, the present disclosure may relate to the following methods:

(a) a method for altering abnormal splicing that contributes to the development or progression of genetic disease in mammalian cells or mammalian individuals, or altering splicing of a pre-mRNA of the mutant IKBKAP gene having the IVS20$^{+6T \rightarrow C}$ mutation in human cells or human individuals;

(b) a method for increasing the ratio of wild-type splicing to abnormal splicing that contributes to the development or progression of genetic disease in mammalian cells or mammalian individuals, or increasing the ratio of wild-type splicing to abnormal splicing of a pre-mRNA of the mutant IKBKAP gene having the IVS20$^{+6T \to C}$ mutation in human cells or human individuals; and (c) a method for increasing the proportion of exon 20 present in an mRNA that is transcribed from a mutant IKBKAP gene having the IVS20$^{+6T \to C}$ mutation in human cells or human individuals.

The methods (a) to (c) may be performed by bringing the compound expressed by the formula (I) or (I') or the pharmaceutical composition of the present disclosure into contact with the human cells or the human individuals.

In one or more embodiments, the mammalian cells or the human cells of the methods (a) to (c) may include in vivo cells, in vitro cells, or ex vivo cells. In one or more embodiments, the mammalian cells may be human cells. In one or more embodiments, the human cells may be neurons of human. In one or more embodiments, the human cells and the human individuals of the methods (a) to (c) may have the IVS20$^{+6T \to C}$ mutation in the endogenous IKBKAP gene.

In one or more non-limiting embodiments, the compound expressed by the formula (I) or (I') or the pharmaceutical composition of the present disclosure may be brought into contact with in vitro or ex vivo mammalian cells or in vitro or ex vivo human cells by addition of the compound expressed by the formula (I) or (I') or the salt of the compound or the pharmaceutical composition of the present disclosure to a cell culture medium. In one or more non-limiting embodiments, the addition is performed so that the concentration of the compound expressed by the formula (I) or (I') is in the range of 100 nM to 1 mM. In one or more embodiments, the compound expressed by the formula (I) or (I') or the pharmaceutical composition of the present disclosure may be brought into contact with in vivo human cells and human individuals according to the method for use of the pharmaceutical composition as described above.

In yet another aspect, the present disclosure relates to a method for preventing, improving, inhibiting the progression of, and/or treating disease or familial dysautonomia (FD) in which abnormal splicing contributes to the development or progression of the disease. The method includes administering the pharmaceutical composition of the present disclosure to a subject in need thereof. In one or more embodiments, examples of the subject include the following: people affected by the disease; people carrying a mutant gene that causes a genetic disease in which abnormal splicing contributes to the development or progression of the genetic disease; FD patients; and people carrying a mutant IKBKAP gene having the IVS20$^{+6T \to C}$ mutation. In one or more embodiments, the pharmaceutical composition of the present disclosure may be administered according to the method for use of the pharmaceutical composition as described above.

Therefore, the present disclosure may further relate to one or more embodiments below.

[A1] A compound expressed by the following formula (I) or (I') or prodrugs or pharmaceutically acceptable salts thereof

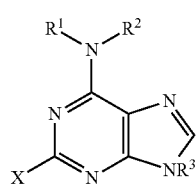

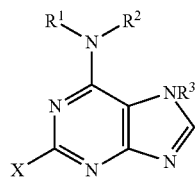

(where, in the formulas (I) and (I'), $R^1$ and $R^2$ each independently represent a hydrogen atom, a linear, branched, or cyclic alkyl group having 1 to 6 carbon atoms, a benzyl or heteroarylmethyl group, a substituted or unsubstituted aryl group, or a substituted or unsubstituted heteroaryl group, $R^3$ represents a hydrogen atom, a linear, branched, or cyclic alkyl group having 1 to 6 carbon atoms, a benzyl or heteroarylmethyl group, a substituted or unsubstituted aryl group, a substituted or unsubstituted heteroaryl group, or $CH_2OC(O)R^4$—, $R^4$ represents a linear, branched, or cyclic alkyl group having 1 to 6 carbon atoms, a benzyl or heteroarylmethyl group, a substituted or unsubstituted aryl group, or a substituted or unsubstituted heteroaryl group, and X represents a hydrogen atom, a halogen atom, an amino group, a $R^1$ and $R^2$ substituted amino group, an azide group, a cyano group, a nitro group, a hydroxyl group, a linear, branched, or cyclic alkyloxy group having 1 to 6 carbon atoms, a substituted or unsubstituted aryloxy group, a substituted or unsubstituted heteroaryloxy group, a mercapto group, a linear, branched, or cyclic alkylthio group having 1 to 6 carbon atoms, a substituted or unsubstituted arylthio group, a substituted or unsubstituted heteroarylthio group, a linear, branched, or cyclic alkyl group having 1 to 6 carbon atoms, a benzyl or heteroarylmethyl group, a substituted or unsubstituted aryl group, or a substituted or unsubstituted heteroaryl group).

[A2] A pharmaceutical composition containing the compound or the prodrugs or the pharmaceutically acceptable salts thereof according to [A1] as an active ingredient.

[A3] The pharmaceutical composition according to [A2] for:

altering abnormal splicing that contributes to genetic disease in mammalian cells or mammalian individuals, or altering splicing of a pre-mRNA of the mutant IKBKAP gene having the IVS20$^{+6T \to C}$ mutation in human cells or human individuals;

increasing the ratio of wild-type splicing to abnormal splicing that contributes to genetic disease in mammalian cells or mammalian individuals, or increasing the ratio of wild-type splicing to abnormal splicing of a pre-mRNA of the mutant IKBKAP gene having the IVS20$^{+6T \to C}$ mutation in human cells or human individuals; or increasing the proportion of exon 20 present in an mRNA that is transcribed from a mutant IKBKAP gene having a IVS20$^{+6T \to C}$ mutation in human cells or human individuals.

[A4] The pharmaceutical composition according to [A3], wherein the cells are neurons.

[A5] The pharmaceutical composition according to any one of [A2] to [A4] for preventing, improving, inhibiting the progression of, and/or treating genetic disease in which abnormal splicing contributes to the development or progression of the disease.

[A6] The pharmaceutical composition according to [A5], wherein the abnormal splicing results from a genetic mutation in a gene to be spliced.

[A7] The pharmaceutical composition according to [A6], wherein the genetic disease is familial dysautonomia (FD).

[A8] A method for altering abnormal splicing that contributes to genetic disease in mammalian cells or mammalian individuals, or altering splicing of a pre-mRNA of the mutant IKBKAP gene having the IVS20$^{+6T \to C}$ mutation in human cells or human individuals, a method for increasing the ratio of wild-type splicing to abnormal splicing that contributes to genetic disease in mammalian cells or mammalian individuals, or increasing the ratio of wild-type splicing to abnormal splicing of a pre-mRNA of the mutant IKBKAP gene having the IVS20$^{+6T \to C}$ mutation in human cells or human individuals, or a method for increasing the proportion of exon 20 present in an mRNA that is transcribed from a mutant IKBKAP gene having the ICVS20$^{+6T \to C}$ mutation in human cells or human individuals, the method including:

bringing the compound or the prodrugs or the pharmaceutically acceptable salts thereof according to [A1], or the pharmaceutical composition according to any one of [A2] to [A7] into contact with mammalian cells, human cells, mammalian individuals, or human individuals.

[A9] A method for altering abnormal splicing that contributes to genetic disease in mammalian individuals, or altering splicing of a pre-mRNA of the mutant IKBKAP gene having the WS20$^{+6T \to C}$ mutation in human individuals, a method for increasing the ratio of wild-type splicing to abnormal splicing that contributes to genetic disease in mammalian individuals, or increasing the ratio of wild-type splicing to abnormal splicing of a pre-mRNA of the mutant IKBKAP gene having the IVS20$^{+6T \to C}$ mutation in human individuals, or a method for increasing the proportion of exon 20 present in an mRNA that is transcribed from a mutant IKBKAP gene having the IVS20$^{+6T \to C}$ mutation in human individuals, the method including:

administering the pharmaceutical composition according to any one of [A2] to [A7] to the individuals.

[A10] The method according to [A7] or [A8], wherein the abnormal splicing results from a genetic mutation in a gene to be spliced.

[A11] A method for preventing, improving, inhibiting the progression of and/or treating genetic disease or familial dysautonomia in which abnormal splicing contributes to the development or progression of the disease, the method including:

administering the pharmaceutical composition according to any one of [A2] to [A7] to a subject in need thereof.

[A12] Use of the compound or the prodrugs or the pharmaceutically acceptable salts thereof according to [A1], or the pharmaceutical composition according to any one of [A2] to [A7] in the method according to any one of [A8] to [A11].

[A13] Use of the compound or the prodrugs or the pharmaceutically acceptable salts thereof according to [A1] in manufacture of the pharmaceutical composition according to any one of [A2] to [A7].

[Splicing Reporter DNA Construct]

In another aspect, the present disclosure relates to a splicing reporter DNA construct that is fused, arranged, or constructed so as to express different reporter genes for a wild-type splice variant and an abnormal splice variant that contributes to the development or progression of disease.

In one or more embodiments, the "abnormal splicing that contributes to the development or progression of disease" of the present disclosure may be, e.g., alternative splicing in disease, disease-specific alternative splicing, alternative splicing that occurs more frequently in disease than normal, or alternative splicing that contributes to the development or progression of disease. Examples of the disease include genetic disease, cancer, and infectious disease.

In one or more non-limiting embodiments, the abnormal splicing that contributes to the development or progression of genetic disease may be abnormal splicing that results from a genetic mutation in a gene to be spliced. In another one or more embodiments, the abnormal splicing that contributes to the development or progression of genetic disease may be splicing of a pre-mRNA of the mutant IKBKAP gene having the IVS20$^{+6T \to C}$ mutation that causes familial dysautonomia (FD) (see the above description and FIG. 1A). Many genetic diseases other than FD are known to be caused by abnormal splicing.

Figure 5:
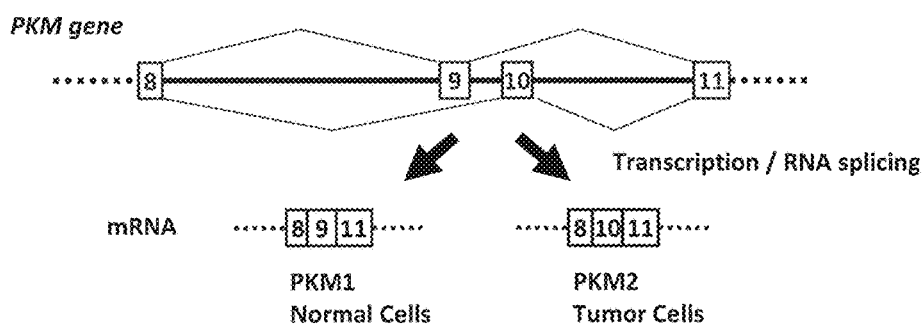
FIG. 5 is a schematic diagram illustrating mutually exclusive splicing of exons 9 and 10 of the pyruvate kinase M (PKM) gene. The PKM2 isoform in which exon 10 is retained is expressed in most cancers.

In one or more non-limiting embodiments, the abnormal splicing that contributes to the development or progression of cancer may be splicing in which PKM2 isoform (exon 10) is selected from mutually exclusive splicing of exons 9 and 10 of a pyruvate kinase M(PKM) gene (see the above description and FIG. 5). The PKM2 is expressed in most cancers and is considered to contribute to the growth of tumors. There may be alternative splicing that contributes to the development of progression of cancer other than the PKM gene.

In one or more non-limiting embodiments, the abnormal splicing that contributes to the development or progression of infectious disease is known as alternative splicing that leads to the switching of the expression of promyelocytic leukemia (PML) isoforms in the cells infected with herpes simplex virus type 2 (HSV-2) (Nojima et al., Nucleic Acids Research, 2009). In one or more non-limiting embodiments, the infectious disease may be caused by viruses, bacteria, fungi, or parasites.

In one or more embodiments, the mammalian cells or the human cells of this embodiment may include in vivo cells, in vitro cells, or ex vivo cells. In one or more embodiments, the mammalian cells may be human cells or cells of mammals other than human. In one or more embodiments, the cells may be neurons, cancer cells, or infected cells.

In one or more embodiments, a splicing reporter DNA construct of the present disclosure is a DNA construct that may function as a splicing reporter that can detect abnormal splicing in a gene region having the IVS20$^{+6T \to C}$ mutation. In one or more embodiments, the DNA construct of this embodiment includes a gene that contains an exon a of 3n+1 or 3n+2 bases in length and an intron having the IVS20$^{+6T \to C}$ mutation in the IKBKAP gene, and two different reporter genes, and the DNA construct is fused, arranged, or constructed so as to express different reporter genes for a wild-type splice variant containing the exon a and an abnormal splice variant in which the exon a is skipped.

In another one or more embodiments, a reporter construct of this embodiment includes a region from exon 19 to exon 21 of the human IKBKAP gene having the IVS20$^{+6T \to C}$ mutation, and two different reporter genes, and the reporter construct is fused, arranged, or constructed so as to express different reporter genes for a wild-type splice variant containing exon 20 and an abnormal splice variant in which exon 20 is skipped. In one or more embodiments, a portion of exon 19 and/or a portion of exon 21 may be deleted if they are located in the range where exon 20 is skipped by abnormal splicing in the region from exon 19 to exon 21.

In one or more non-limiting embodiments, the reporter genes in the DNA construct of this embodiment may be various fluorescent protein genes.

Figure 1B:
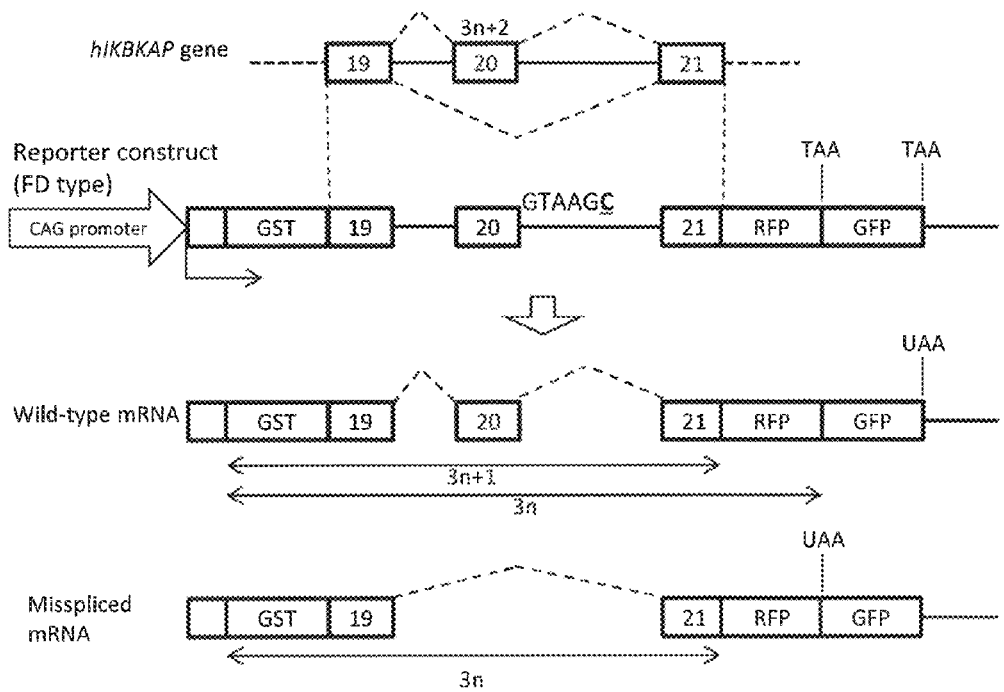
FIG. 1B is a diagram illustrating one or more embodiments of a splicing reporter DNA construct. This construct is produced by subcloning a part of the normal human IKBKAP genomic region with the IVS20$^{+6T \to C}$ mutation. When the construct undergoes wild-type splicing, the RFP coding region and its stop codon (UAA) are out-of-frame, and the GFP coding region is translated in-frame. On the other hand, when the construct undergoes abnormal splicing, the RFP gene and the stop codon (UAA) of the RFP gene are translated in-frame.

In one or more non-limiting embodiments, the DNA construct of this embodiment can be described using a reporter construct as illustrated in FIG. 1B. In the DNA construct of FIG. 1B, a gene for a GST protein, exons 19 to 21 of a mutant human IKBKAP gene, a red fluorescent protein (RFP), and a green fluorescent protein (GFP) are connected in this order downstream of a CAG promoter. When this DNA construct undergoes wild-type splicing, the gene for a GST protein and exons 19 to 21 of the mutant human IKBKAP gene are joined to form an mRNA of 3n+1 bases in length, and a stop codon (UAA) of the RFP gene is out-of-frame, so that the GFP gene is translated in the frame to express a green fluorescent protein. On the other hand, when this DNA construct undergoes abnormal splicing, the gene for a GST protein and exons 19 to 21 of the mutant human IKBKAP gene are joined to form an mRNA of 3n bases in length, so that the RFP gene and the stop codon (UAA) of the RFP gene are translated in the frame to express a red fluorescent protein.

Figure 6:
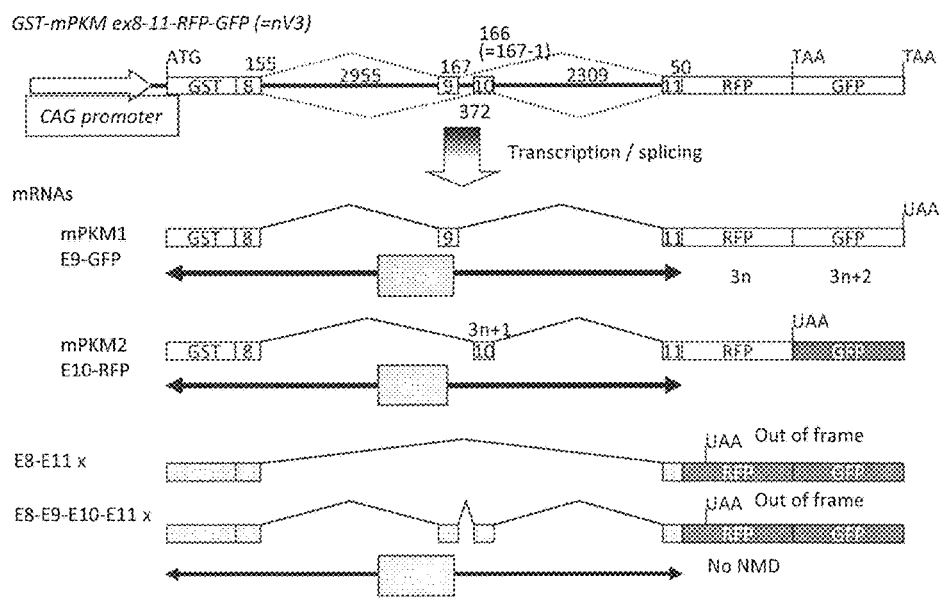
FIG. 6 is a diagram illustrating one or more embodiments of a splicing reporter DNA construct. The genomic region from exon 8 to exon 11 of the PKM gene is linked to RFP, GFP, and cDNA that are connected so as to change the frame. The DNA construct is designed so that (i) the frame is adjusted to GFP when exon 9 is selected, (ii) the frame is adjusted to RFP when exon 10 is selected, and (iii) the frame is adjusted to neither RFP nor GFP when both exons 9 and 10 are not selected and skipped or when both exons 9 and 10 are selected.

In one or more embodiments, the splicing reporter DNA construct of the present disclosure is fused, arranged, or constructed so as to express different reporter genes by mutually exclusive splicing of exons 9 and 10 of a PKM gene. In one or more non-limiting embodiments, the DNA construct of this embodiment can be described using a reporter construct as illustrated in FIG. 6. A genomic region from exon 8 to exon 11 of the PKM gene is linked to RFP, GFP, and coding regions are connected so as to change the frame. The reporter construct is designed so that (i) the frame is adjusted to GFP when exon 9 is selected, (ii) the frame is adjusted to RFP when exon 10 is selected, and (iii) the frame is adjusted to neither the RFP nor the GFP when both exons 9 and 10 are not selected and skipped or when both exons 9 and 10 are selected.

A method for producing the splicing reporter DNA construct of the present disclosure can be explained by referring to WO 2011/152043 A1. The entire contents of this document are incorporated into the present disclosure by reference.

[Method for Testing Whether or not Abnormal Splicing is Inhibited]

When the reporter DNA construct of the present disclosure is introduced into cells, the cells can be used to test whether a substance that has been in contact with the cells can inhibit abnormal splicing. Therefore, in another aspect, the present disclosure relates to a method for screening a substance capable of inhibiting abnormal splicing that contributes to the development or progression of disease, the method including:

(A) introducing the splicing reporter DNA construct of the present disclosure into eukaryotic cells or eukaryotes so that the eukaryotic cells or the eukaryotes, into which the DNA construct has been introduced, are optionally used as conditions for the abnormal splicing to occur;

(B) contacting or expressing a test substance with or in the eukaryotic cells or the eukaryotes;

(C) detecting at least one of wild-type splicing and abnormal splicing by expression of the reporter genes; and (D) determining whether the ratio of the expression of the reporter gene by wild-type splicing to the expression of the reporter gene by abnormal splicing is changed as compared to the control that does not contact with or express the test substance.

In one or more embodiments, the eukaryotic cells or eukaryotes may be mammalian or human cells or mammalian or human individuals. In one or more embodiments, the screening method of the present disclosure may use in vivo cells, in vitro cells, or ex vivo cells. In one or more embodiments, the mammalian cells may be human cells. In one or more embodiments, the cells may be neurons, cancer cells, or infected cells.

In one or more non-limiting embodiments, "the eukaryotic cells or the eukaryotes, into which the DNA construct has been introduced, are used as conditions for the abnormal splicing to occur" means that the oxygen concentration is set to 0.5%, and oligomycin (ATP synthase inhibitor) is allowed to be present so that the same conditions of tumor cells are created.

In one or more embodiments, when the test substance is a protein, an expression vector of cDNA that encodes this protein may be further introduced into the eukaryotic cells or the eukaryotes, into which the splicing reporter DNA construct of the present disclosure has been introduced, so that the test substance is expressed. In one or more embodiments, the test substance may be expressed by introducing a vector that can express the test substance into the eukaryotic cells or the eukaryotes. In one or more embodiments, a gene expression library or an expression vector that incorporates cDNA may be appropriately used as the vector. On the other hand, in one or more embodiments, when the test substance is a low molecular compound, the eukaryotic cells or the eukaryotes, into which the splicing reporter DNA construct of the present disclosure has been introduced, may be cultured in the presence of the low molecular compound, so that the test substance is brought into contact with the eukaryotic cells or the eukaryotes.

In one or more embodiments, the screening method of the present disclosure is a method for screening a candidate compound that is to be an active ingredient of a pharmaceutical composition for disease in which abnormal splicing contributes to the development or progression of the disease. As described above, in one or more embodiments, the disease in which abnormal splicing contributes to the development or progression of the disease may be, e.g., genetic disease, cancer, or infectious disease. In one or more non-limiting embodiments, the genetic disease may be, e.g., familial dysautonomia (FD).

Therefore, in another one or more embodiments, the screening method of the present disclosure is a method for testing whether a substance inhibits abnormal splicing that results from the $IVS20^{+6T \rightarrow C}$ mutation in the IKBKAP gene, the method including:

(A) introducing the reporter DNA construct of the present disclosure into eukaryotic cells or eukaryotes;

(B) contacting or expressing a substance to be tested with or in the eukaryotic cells or the eukaryotes;

(C) detecting at least one of wild-type splicing and abnormal splicing by expression of the reporter genes; and (D) determining whether the ratio of the expression of the reporter gene by wild-type splicing to the expression of the reporter gene by abnormal splicing is changed as compared to the control that does not contact with the substance to be tested.

In one or more embodiments, the detection of at least one of wild-type splicing and abnormal splicing by the expression of the reporter genes in step (C) of the screening method of the present disclosure is not particularly limited and may be appropriately selected depending on the reporter gene, e.g., from a fluorescent signal detection and RT-PCR.

In one or more embodiments of step (D) of the screening method of the present disclosure, if the ratio of wild-type splicing in the cells that have been in contact with the test substance is increased, the test substance can be selected as a candidate substance capable of inhibiting abnormal splicing.

In another one or more embodiments, the test substance may be a low molecular compound. Therefore, in another aspect, the present disclosure relates to a method for screening a low molecular compound capable of inhibiting abnormal splicing that contributes to the development or progression of disease, the method including:

(A) introducing the splicing reporter DNA construct of the present disclosure into eukaryotic cells or eukaryotes so that the eukaryotic cells or the eukaryotes, into which the DNA construct has been introduced, are optionally used as conditions for the abnormal splicing to occur;

(B) contacting a low molecular compound to be tested with the eukaryotic cells or the eukaryotes;

(C) detecting at least one of wild-type splicing and abnormal splicing by expression of the reporter genes; and (D) determining whether the ratio of the expression of the reporter gene by wild-type splicing to the expression of the reporter gene by abnormal splicing is changed as compared to the control that does not contact with the low molecular compound.

Moreover, the present disclosure relates to a method for screening a low molecular compound capable of inhibiting abnormal splicing that results from the IVS20$^{+6T \to C}$ mutation of the IKBKAP gene, the method including:

(A) introducing the reporter DNA construct of the present disclosure into eukaryotic cells or eukaryotes;

(B) contacting a low molecular compound to be tested with the eukaryotic cells or the eukaryotes;

(C) detecting at least one of wild-type splicing and abnormal splicing by expression of the reporter genes; and (D) determining whether the ratio of the expression of the reporter gene by wild-type splicing to the expression of the reporter gene by abnormal splicing is changed as compared to the control that does not contact with the low molecular compound.

In one or more embodiments of step (D) of the screening method of the present disclosure, if the ratio of wild-type splicing in the cells that have been in contact with the test low molecular compound is increased, the test low molecular compound can be selected as a candidate low molecular compound capable of inhibiting abnormal splicing. Therefore, in another aspect, the present disclosure relates to a pharmaceutical composition for disease in which abnormal splicing contributes to the development or progression of the disease, the pharmaceutical composition containing an active ingredient capable of inhibiting the abnormal splicing.

[Kit]

In another aspect, the present disclosure relates to a kit that includes the splicing reporter DNA construct of the present disclosure and cells that may cause abnormal splicing. The kit can be used in the screening method of the present disclosure. The kit may further include a vector that can express a test substance.

Therefore, the present disclosure may further relate to one or more embodiments below.

[B1] A method for screening a substance capable of inhibiting abnormal splicing that contributes to the development or progression of disease, the method including:

(A) introducing a DNA construct into eukaryotic cells or eukaryotes so that the eukaryotic cells or the eukaryotes, into which the DNA construct has been introduced, are optionally used as conditions for the abnormal splicing to occur, wherein the DNA construct is fused, arranged, or constructed so as to express different reporter genes for a wild-type splice variant and an abnormal splice variant that contributes to the development or progression of disease;

(B) contacting or expressing a test substance with or in the eukaryotic cells or the eukaryotes;

(C) detecting at least one of wild-type splicing and abnormal splicing by expression of the reporter genes; and (D) determining whether the ratio of the expression of the reporter gene by wild-type splicing to the expression of the reporter gene by abnormal splicing is changed as compared to the control that does not contact with or express the test substance.

[B2] The method according to [B1], wherein the test substance is expressed by introducing a vector that can express the test substance into the eukaryotic cells or the eukaryotes.

[B3] The method according to [B1] or [B2], including a method for screening a candidate compound that is to be an active ingredient of a pharmaceutical composition for disease in which abnormal splicing contributes to the development or progression of the disease.

[B4] The method according to any one of [B1] to [B3], wherein the disease is genetic disease, cancer, or infectious disease.

[B5] A method for testing whether a substance inhibits abnormal splicing that results from the IVS20$^{+6T \to C}$ mutation of the IKBKAP gene, the method including:

(A) introducing a DNA construct into eukaryotic cells or eukaryotes, wherein the DNA construct includes a gene that contains an exon a of 3n+1 or 3n+2 bases in length and an intron having the IVS20$^{+6T \to C}$ mutation of the IKBKAP gene, and two different reporter genes, and the gene and the two reporter genes in the DNA construct are fused, arranged, or constructed so as to express different reporter genes for a wild-type splice variant containing the exon a and an abnormal splice variant in which the exon a is skipped;

(B) contacting or expressing a substance to be tested with or in the eukaryotic cells or the eukaryotes;

(C) detecting at least one of wild-type splicing and abnormal splicing by expression of the reporter genes; and (D) determining whether the ratio of the expression of the reporter gene by wild-type splicing to the expression of the reporter gene by abnormal splicing is changed as compared to the control that does not contact with the substance to be tested.

[B6] A pharmaceutical composition for preventing, improving, inhibiting the progression of, and/or treating disease in which abnormal splicing contributes to the development or progression of the disease, the pharmaceutical composition containing an active ingredient capable of inhibiting the abnormal splicing.

[B7] The pharmaceutical composition according to [B6], wherein the disease in which abnormal splicing contributes to the development or progression of the disease is genetic disease, cancer, or infectious disease.

[B8] A DNA construct including:

a gene that contains an exon a of 3n+1 or 3n+2 bases in length and an intron having the IVS20$^{+6T \to C}$ mutation of the IKBKAP gene; and two different reporter genes, wherein the gene and the two reporter genes in the DNA construct are fused, arranged, or constructed so as to express different reporter genes for a wild-type splice variant containing the exon a and an abnormal splice variant in which the exon a is skipped.

[B9] A kit including:

a DNA construct that is fused, arranged, or constructed so as to express different reporter genes for a wild-type splice variant and an abnormal splice variant that contributes to the development or progression of disease; and cells that are may cause abnormal splicing.

[B10] The kit according to [B9], further including a vector that can express a test substance.

EXAMPLES

Hereinafter, the present disclosure will be described in more detail by way of examples, which are for illustrative purposes only. However, the present disclosure is not limited to the examples. All the documents cited in the present disclosure are incorporated herein by reference.

Production Example 1

Production of Compound 1

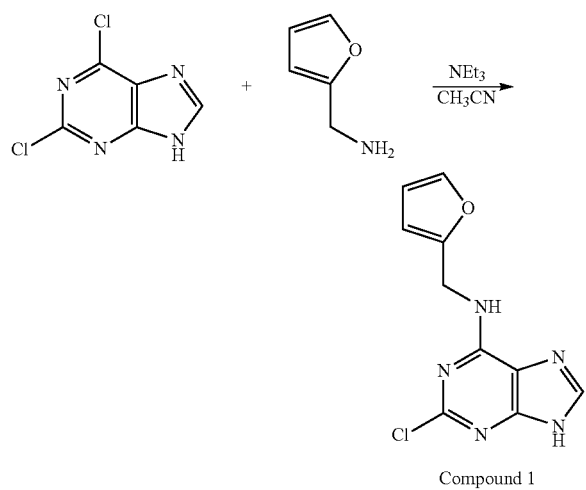

Compound 1

A compound 1 was synthesized in the following manner with reference to the method disclosed in WO 2010/118367.

Triethylamine (0.15 mL, 1.08 mmol) was added at room temperature to an acetonitrile (20 mL) solution including 2,6-dichloro-1H-purine (189 mg, 1.00 mmol, commercial product) and furfurylamine (97.0 mg, 1.00 mmol, commercial product). The mixture was stirred at room temperature for 6 hours, and then stirred at 60° C. for 3 hours. After this mixed solution was concentrated under reduced pressure, water was added to the solution to form white precipitates, and the white precipitates were removed by filtration. The resultant solid was washed with water and subsequently with diethyl ether. Consequently, 2-chloro-N-(2-furanylmethyl)-7H-purin-6-amine (compound 1) (19.8 mg, 0.0795 mmol, 8.0%) was obtained as a white solid. TLC Rf 0.22 (ethyl acetate); $^1$H NMR (DMSO-$d_6$, 400 MHz) δ 4.56-4.67 (br, 2H), 6.24-6.28 (br, 1H), 6.35-6.40 (br, 1H), 7.54-7.57 (br, 1H), 8.11-8.15 (br, 1H), 8.54-8.64 (br, 1H), 13.05-13.17 (br, 1H)

Reference Compound 1

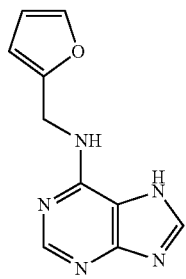

Reference Compound 1

The reference compound 1 was kinetin, which was manufactured by NACALAI TESQUE, INC.

[Production of Two-Color Fluorescent Type Splicing Reporter Construct]

A reporter construct (FD type) as illustrated in FIG. 1B was produced by utilizing exons 19 to 21 of a mutant human IKBKAP gene having the IVS20$^{+6T \to C}$ mutation as illustrated in FIG. 1A. In the reporter construct, a gene for a GST protein, exons 19 to 21 of a mutant human IKBKAP gene, a red fluorescent protein (RFP), and a green fluorescent protein (GFP) were connected in this order downstream of a CAG promoter. When this reporter construct underwent wild-type splicing, the gene for a GST protein and exons 19 to 21 of the mutant human IKBKAP gene were joined to form an mRNA of 3n+1 bases in length, and a stop codon (UAA) of the RFP gene was out-of-frame, so that the GFP gene was translated in the frame to express a green fluorescent protein. On the other hand, when this reporter construct underwent abnormal splicing, the gene for a GST protein and exons 19 to 21 of the mutant human IKBKAP gene were joined to form an mRNA of 3n bases in length, so that the RFP gene and the stop codon (UAA) of the RFP gene were translated in the frame to express a red fluorescent protein.

The use of the reporter construct of FIG. 1B facilitates the determination of whether splicing of the pre-mRNA of the mutant human LEBKAP gene having the IVS20$^{+6T \to C}$ mutation is wild-type splicing or abnormal splicing.

Another reporter construct (wild type) was further produced in the same manner as the reporter construct (FD type) except that a wild-type human IKBKAP gene was used instead of the mutant human IKBKAP gene.

The FD-type reporter construct and the wild-type reporter construct were transfected separately into the HeLa cells in order to check if abnormal splicing in a FD patient was demonstrated.

First, the fluorescence microscopic observation confirmed that GFP was expressed in the cells into which the wild-type reporter construct had been transfected, and thus normal splicing occurred (data not shown). Moreover, the fluorescence microscopic observation confirmed that RFP was expressed in the cells into which the FD-type reporter construct had been transfected, and thus abnormal splicing occurred (data not shown).

Figure 2:
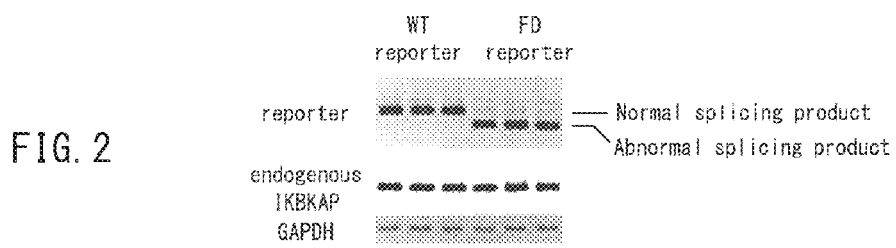
FIG. 2 The wild-type reporter construct and FD-type reporter construct are transfected separately into HeLa cells, and their splicing products are confirmed by RT-PCR.

Further, the results of RT-PCR confirmed that normal splicing products were observed in the cells into which the wild-type reporter construct had been transfected, and that abnormal splicing products were observed in the cells into which the FD-type reporter construct had been transfected, as illustrated in FIG. 2. As the internal control, an mRNA of the endogenous IKBKAP gene and an mRNA of the GAPDH gene were used.

[Screening of Compound for Inhibiting Abnormal Splicing]

The FD-type reporter construct was used to screen a compound capable of inhibiting abnormal splicing of a pre-mRNA that was transcribed from the construct. Specifically, the FD-type reporter construct was transfected into HeLa cells, and then a test compound was brought into contact with the HeLa cells and cultured. Next, fluorescence observation was performed after a predetermined time, and the fluorescence intensity ratio (GFP/RFP) of GFP (normal splicing products) to RFP (abnormal splicing products) was compared to the control (e.g., a solvent alone or kinetin (reference compound 1)), so that the compound with higher fluorescence intensity was determined. Consequently, the compound 1 was selected as a candidate compound for inhibiting abnormal splicing.

[Confirmation of Effect of Inhibiting Abnormal Splicing by Compound 1]

Figure 3:
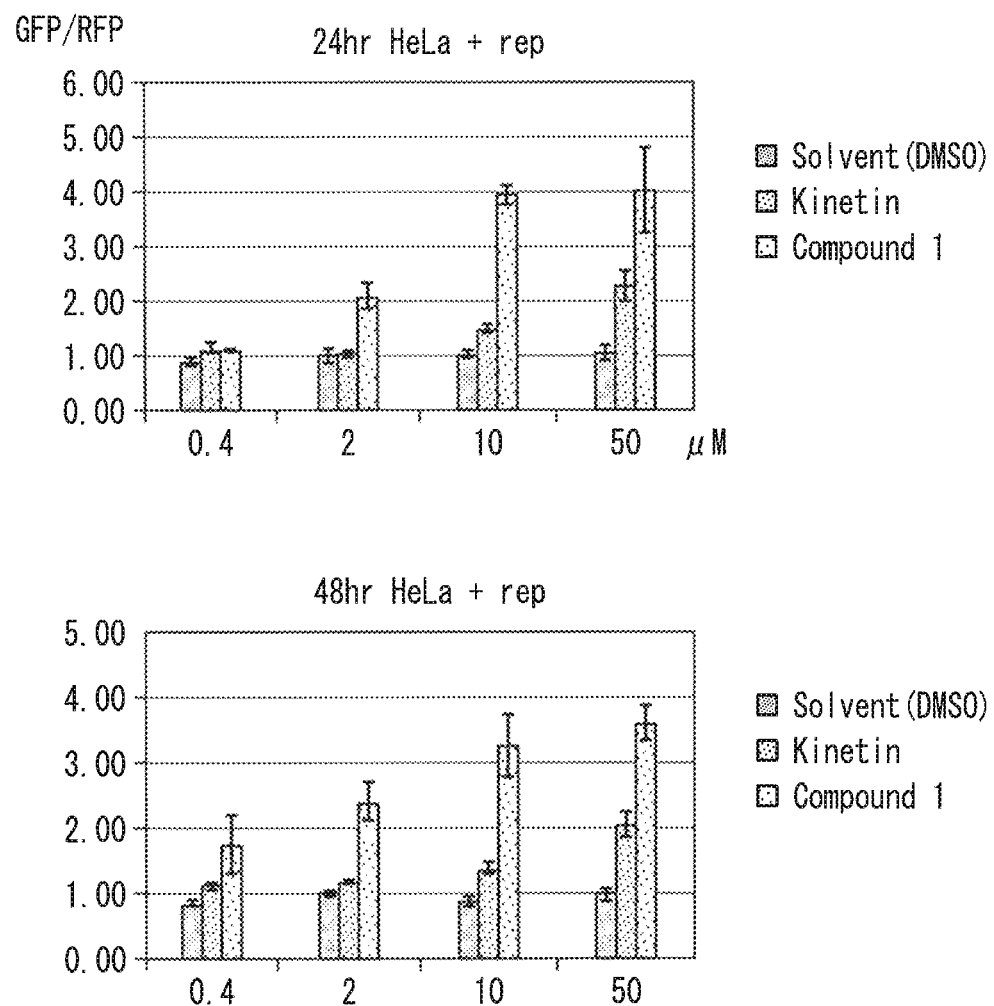
FIG. 3 The HeLa cells, into which the FD-type reporter construct has been transfected, are cultured along with compound 1 (for 24 hours and 48 hours), and then the fluorescence signal ratio (GFP/RFP) of GFP (normal splicing) to RFP (abnormal splicing) is determined for each after 24 hours and 48 hours.

The FD-type reporter construct was transfected into HeLa cells, and then the compound 1 was brought into contact with the HeLa cells and cultured (compound concentration: 0.4, 2.0, 0.10, and 50.0 μM). Next, fluorescence observation was performed each after 24 hours and 48 hours, and the fluorescence intensity ratio (GFP/RFP) was determined. FIG. 3 illustrates the results.

The graphs of FIG. 3 illustrate the relationship between the administration concentration and the fluorescence intensity ratio (GFP/RFP) of the control (solvent alone), kinetin, and compound 1. As illustrated in FIG. 3, the fluorescence intensity ratio (GFP/RFP) of the compound 1 increased in a concentration-dependent manner, and the degree of increase was significantly higher than that of the kinetin. This shows that compound 1 was capable of inhibiting abnormal splicing that results from the IVS20$^{+6T \rightarrow C}$ mutation more effectively than the kinetin.

[Confirmation of Effect of Inhibiting Abnormal Splicing by Compound 1 in Cell of FD Patient]

The cells of FD patients were obtained from Coriell Institute. The endogenous IKBKAP gene in the cells of FD patients had the IVS20$^{+6T \rightarrow C}$ mutation.

Figure 4:
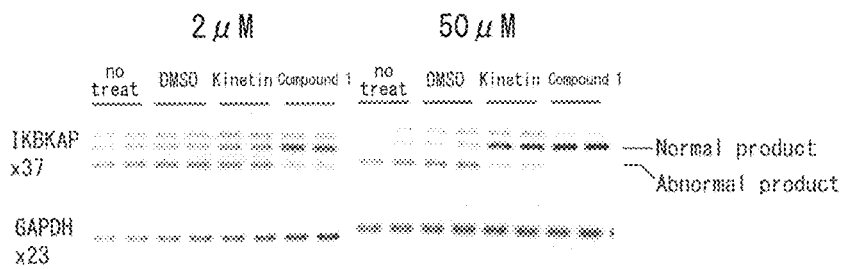
FIG. 4 The cells of FD patients are cultured along with compound 1 (for 60 hours), and then the spliced products (mRNAs) of the endogenous IKBKAP gene in the cells of FD patients are confirmed by RT-PCR.

Compound 1 and the kinetin were added at a concentration of 2 μM or 50 μM to a culture medium of the cells of FD patients. The cells were cultured for 60 hours, collected, and then subjected to RT-PCR. As the control, untreated cells and DMSO (solvent) treated cells were used. FIG. 4 illustrates the results.

As illustrated in FIG. 4, compound 1 was capable of inhibiting abnormal splicing at a concentration as low as 2 μM. The abnormal splicing inhibition activity of compound 1 was about the same as that of the kinetin at a concentration of 50 μM.

The invention claimed is:

1. A pharmaceutical composition containing a compound expressed by the following formula (I) or (I') or the pharmaceutical acceptable salts thereof as an active ingredient useful in a method of altering splicing of a pre-mRNA of a mutant IKBKAP gene having a IVS20+6T-C mutation in human cells or human individuals; increasing a ratio of wild-type splicing to abnormal splicing of a pre-mRNA of a mutant IKBKAP gene having a IVS20+6T-C mutation in human cells or human individuals; or increasing a proportion of exon 20 present in an mRNA that is transcribed from a mutant IKBKAP gene having a IVS20+6T-C mutation in human cells or human individuals,

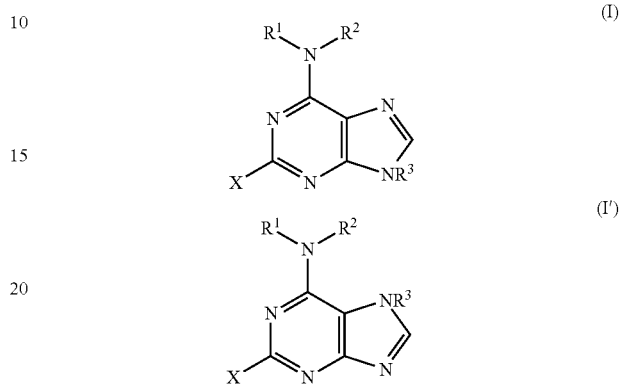

wherein, in the formulas (I) and (I'),
$R^1$ represents a heteroarylmethyl group,
$R^2$ represents a hydrogen atom,
$R^3$ represents a hydrogen atom and
X represents a halogen atom.

2. The pharmaceutical composition according to claim 1, wherein the cells are neurons, cancer cells, or infected cells.

3. The pharmaceutical composition according to claim 1, for preventing, improving, inhibiting progression of, and/or treating genetic disease.

4. The pharmaceutical composition according to claim 1, wherein the halogen atom is a fluorine atom or a chlorine atom.

5. The pharmaceutical composition according to claim 1, wherein the compound is the compound expressed by the following formula (II):

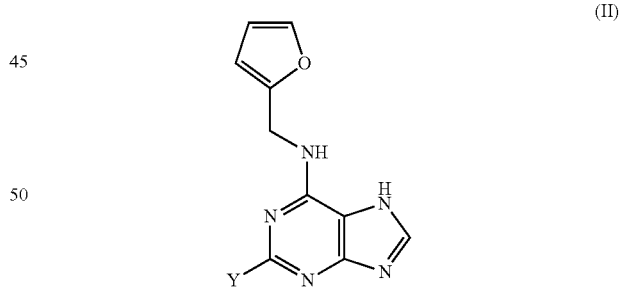

wherein Y represents a halogen atom.

* * * * *